(12) United States Patent
Smart et al.

(10) Patent No.: US 9,377,468 B2
(45) Date of Patent: Jun. 28, 2016

(54) ION MOBILITY MASS SPECTROMETRY TAGS FOR QUANTITATIVE APPLICATIONS AND METHODS THEREOF

(71) Applicant: Agilent Technologies, Inc., Loveland, CO (US)

(72) Inventors: Brian Phillip Smart, San Jose, CA (US); Joel Myerson, Berkeley, CA (US); Craig Daniel Wenger, Sunnyvale, CA (US); Javier E. Satulovsky, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 169 days.

(21) Appl. No.: 14/209,362

(22) Filed: Mar. 13, 2014

(65) Prior Publication Data
US 2014/0273252 A1 Sep. 18, 2014

Related U.S. Application Data

(60) Provisional application No. 61/800,186, filed on Mar. 15, 2013.

(51) Int. Cl.
*G01N 33/68* (2006.01)

(52) U.S. Cl.
CPC ........ *G01N 33/6848* (2013.01); *G01N 2458/15* (2013.01); *Y10T 436/13* (2015.01); *Y10T 436/142222* (2015.01); *Y10T 436/24* (2015.01)

(58) Field of Classification Search
CPC .............. G01N 33/68; G01N 33/6848; G01N 2458/00; G01N 2458/15; Y10T 436/13; Y10T 436/14; Y10T 436/141111; Y10T 436/142222; Y10T 436/145555; Y10T 436/147777; Y10T 436/17; Y10T 436/173845; Y10T 436/20; Y10T 436/200833; Y10T 436/203332; Y10T 436/21; Y10T 436/216; Y10T 436/24
USPC ........... 436/91, 92, 93, 96, 98, 106, 111, 127, 436/128, 131, 139, 142, 173, 86, 89, 56; 530/300; 548/526
See application file for complete search history.

(56) References Cited

PUBLICATIONS

Bohrer et al. Analytical Chemistry, vol. 83, May 24, 2011, pp. 5377-5385.*
Franski et al. International Journal of Mass Spectrometry, vol. 266, Jul. 21, 2007, pp. 180-184.*
Hilderbrand, et al., "Exploring Crown Ethers as Shift Reagents for Ion Mobility Spectrometry", Anal Chem., 2006, 78(19): 6792-6800.
Julian, et. al., "Molecular recognition of arginine in small peptides by supramolecular complexation with dibenzo-30-crown-10 ether", International Journal of Mass Spectrometry, 220, 2002, 87-96.

* cited by examiner

*Primary Examiner* — Maureen Wallenhorst

(57) ABSTRACT

Compound tags and shifting agents are provided that find use in ion mobility spectrometry (IMS), mass spectrometry (MS), or a combination of IMS and MS, and which can substantially increase separation of multiple components in complex samples and facilitate quantitative and multiplexed analyses. In some cases, the compounds include a linker and a normalizing group, each including a structural unit and separated by a cleaveable group, and a crown ether. Also provided are methods for analyzing peptides in a sample. In some cases, the method includes coupling the compound to peptides which include a terminal guanidinium moiety capable of forming an intra-molecular complex with the crown ether.

20 Claims, 8 Drawing Sheets

ION MOBILITY MASS SPECTROMETRY TAGS FOR QUANTITATIVE APPLICATIONS AND METHODS THEREOF

CROSS REFERENCE TO RELATED APPLICATION

This application claims the benefit of U.S. Provisional Application No. 61/800,186, filed Mar. 15, 2013, the disclosure of which is herein incorporated by reference in its entirety.

INTRODUCTION

Ion mobility spectrometry (IMS)-mass spectrometry (MS) has become a valuable tool that helps with rapid separation and analysis and characterization of complex samples with multiple components on a millisecond timescale. IMS-MS involves a hyphenated separation or multi-dimensional separation, in which an ion mobility spectrometer first separates ions according to their mobilities followed by a second step where the mass spectrometer separates ions according to their mass-to-charge ratio.

While IMS-MS technique has gained usage in proteomics for the analysis of peptides, detection of specific analytes, analysis of nanoparticles, etc., quantification and multiplexing remain significant challenges for conventional IMS-MS. For example, in proteomics analyses, quantification is often crucial in providing timely and practical analytical results. IMS exploits the differences of particles in diffusion through a gas at different speeds, depending on their collision cross sections with the gas molecules. Due to the similarities of many analytes in their cross section profiles, it remains challenging to resolve complex components based on exiting IMS techniques while allowing quantitative characterizations of multiple components.

Thus, there remains an ongoing need for methods that enable quantitative and multiplexed analyses of complex samples.

SUMMARY

The invention generally relates to compositions and methods for ion mobility spectrometry-mass spectrometry. More particularly, the invention relates to covalent tags and shifting agents, complexes formed therefrom, and related compositions and methods of preparation and uses. Compound tags and shifting agents are provided that find use in ion mobility spectrometry (IMS), mass spectrometry (MS), or a combination of IMS and MS, and which can substantially increase separation of multiple components in complex samples and facilitate quantitative and multiplexed analyses. In some cases, the compounds include a linker and a normalizing group, each including a structural unit and separated by a cleaveable group, and a crown ether. Also provided are methods for analyzing peptides in a sample. In some cases, the method includes coupling the compound to peptides which include a terminal guanidinium moiety capable of forming an intra-molecular complex with the crown ether.

DEFINITIONS

Figure 1:
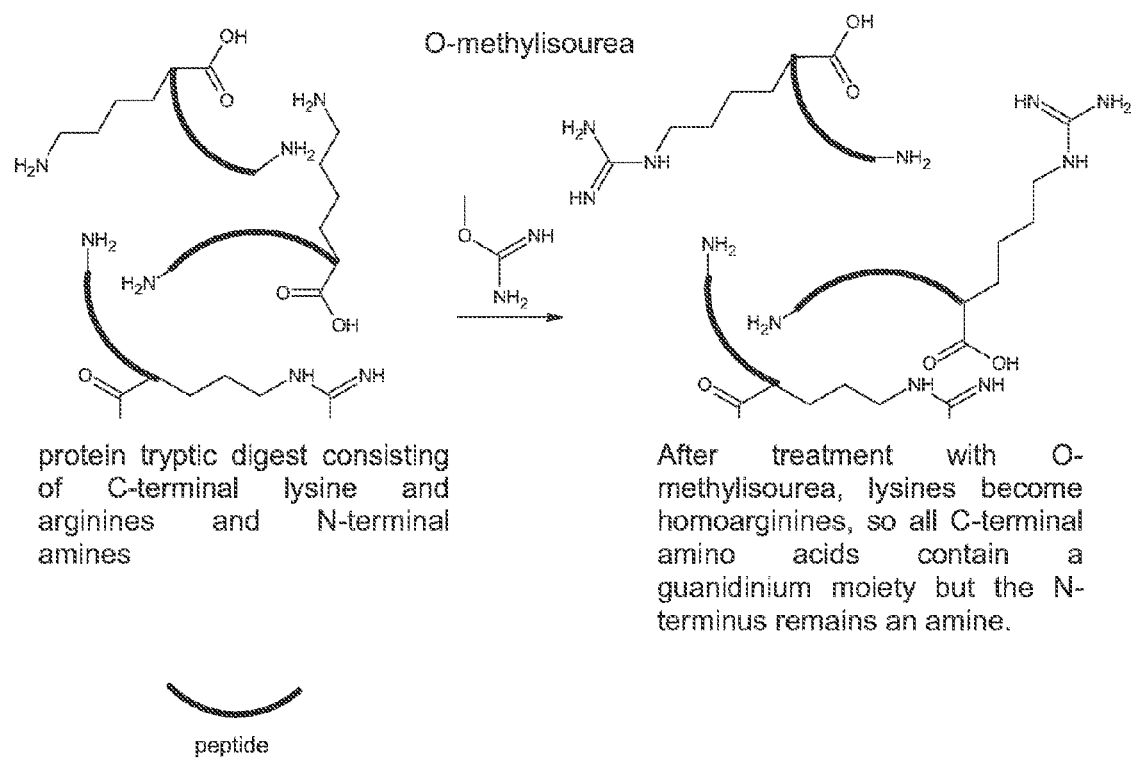
FIG. 1 shows a schematic illustration of an exemplary embodiment of the subject methods, including protein tryptic digest and treatment with O-methylisourea to convert lysine residues to homoarginines.

Unless defined otherwise, all technical and scientific terms used herein have the same meaning as commonly understood by one of ordinary skill in the art to which this invention belongs. Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Sambrook et al., Molecular Cloning: A Laboratory Manual, 2nd Edition (Cold Spring Harbor Laboratory, 1989); and the like. Still, certain terms are defined below for the sake of clarity and ease of reference.

The term "alkyl", as used herein, refers to a saturated straight chain, branched or cyclic hydrocarbon group (e.g., having 1 to 24, typically 1 to 12) carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. Alkyls include "cycloalkyls", which refer to cyclic alkyl groups such as cyclopropyl, cyclobutyl, cyclopentyl, cyclohexyl, cycloheptyl and cyclooctyl.

The term "alkylene", as used herein, refers to a straight, branched chain or cyclic divalent radicals having up to 50 carbons, unless the chain length or ring size is limited thereto. Typical examples include methylene (—CH$_2$—), ethylene (—CH$_2$CH$_2$—), hexylene, heptylene, octylene, nonylene, and decylene, among others.

The term "amino", as used herein, refers to the group —NR'R" (or NRR'R") where R, R' and R" are independently selected from the group consisting of hydrogen, alkyl, substituted alkyl, aryl, substituted aryl, arylalkyl, substituted arylalkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —NRR'R" and its biologically compatible anionic counterions.

The term "amino acid", as used herein, refers to not only the L, D- and nonchiral forms of the common naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, epsilon-nicotinoyl-lysine, isonipecotic acid, tetrahydroisoquinoleic acid, sarcosine, citrulline, cysteic acid, t-butylglycine, t-butylalanine, phenylglycine, cyclohexylalanine, beta-alanine, 4-aminobutyric acid, and the like.

The term "biomolecule" may refer to a compound found in nature, a derivative of a compound found in nature, a synthetically modified analog of a compound found in nature, a genetically engineered analog of a compound found in nature, a genetically engineered modified analog of a compound found in nature. For example, biomolecules may be and/or include peptides, proteins; antibodies; antibody-fragments; haptens; glycoproteins; cell-membrane proteins; enzymes, such as alkaline phosphatase, beta-galactosidase, horseradish peroxidase, or urease; peptides; peptide nucleic acids (PNAs); locked nucleic acids (LNAs); genetically engineered peptides; genetically engineered proteins; genetically engineered antibodies; genetically engineered antibody-fragments; oligonucleotides; RNA; DNA; saccharide-containing molecules; monosaccharides; disaccharides; trisaccharides; oligosaccharides; polysaccharides, such as dextran; small molecules, including drug-like molecules; drugs; antigens, such as tumor antigens; pathogens; toxins; polymers, including biopolymers and/or dendrimers; nuclear receptors; nuclear receptor substrates and/or ligands; cytokines; epitopes, including peptide epitopes, antigen epitopes, and/or pathogen epitopes; enzyme substrates; and/or combinations or derivatives thereof.

The term "cleavable group" or "cleavable moiety", as used herein, refers to a linker that can be selectively cleaved to produce two products. Application of suitable cleavage conditions to a molecule having a cleavable group or moiety will produce two products. A cleavable group or moiety of the present invention is stable until it is contacted with a cleavage-inducing stimulus resulting in cleavage or dissociation of the molecule.

The term "complex", as used herein, refers to the association of two or more molecules, or two or more moieties in a molecule, usually by non-covalent bonding.

The term "crown ether", as used herein, refers to a linear or macrocyclic chelating ligand. Crown ethers include, but are not limited to, those described by C. J. Pedersen (J. Am. Chem. Soc. 1967, 89, 7017) and analogs and derivatives thereof, such as those ligands that include the replacement of one or more of the ring's oxygen atoms with nitrogen atoms resulting in azacrown ethers and/or the attachment of one or more side chains to the ring to form a so-called lariat or armed crown ether. Numerous publications on the ion-complexing properties of diazacrown ethers containing side chains attached to the nitrogen atoms of the macrocycle (see e.g. Chi et al, Bull. Korean Chem. Soc. (2002) 23(5) 688-692; Gonzalez-Lorenzo et al, Inorg Chem. (2005) 44(12): 4254-4262; Wang et al., Chinese Chemical Letters, (2003) 14(6): 579-580; Peters et al, J. Chem. Soc., Dalton Trans., (2000) 4664-4668; and I. A. Fallis, Annu. Rep. Prog. Chem. A 94 (1998) 351-387). In some instances, crown ether refers to a cyclic polyether comprised of repeating units of —$CH_2CH_2O$—. The number of —$CH_2CH_2O$— may be 4, 5, 6, 10, etc. Examples of crown ethers include, but are not limited to, 12-crown-4,15-crown-5, and 18-crown-6,30-crown-10, and derivatives thereof. A crown ether may include one or more heteroatoms such as O, N and/or S in the cyclic backbone, e.g., diaza-18-crown-6, cryptands. In some cases, the term "crown ether" includes linear oligomers comprised of repeating units of —$CH_2CH_2O$— having the ability to complex cations.

The term "diamine" as used herein refers to a reagent comprising two amino groups independently selected from a primary and a secondary amino group. Examples of diamines include, 1,2-diaminoethane (ethylene diamine), 1,4-diaminobutane, N-ethyl-1,2-diaminoethane, 2,2'-diaminodiethylamine, and the like.

The term "ethylene-oxide unit", as used herein, refers to a unit of —$CH_2CH_2O$—.

The term "ethylene diamine unit", as used herein, refers to a unit of —$NHCH_2CH_2NH$—.

The term "ligand", as used herein, refers to a moiety that is capable of binding a compound or moiety of interest. In some cases, a first ligand and a second ligand form a complex by specifically binding to each other.

The term "linker", as used herein, refers to a linking moiety that connects two groups and has a backbone of 20 atoms or less in length. A linker or linkage may be a covalent bond that connects two groups or a chain of between 1 and 20 atoms in length, for example of about 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, oligo(ethylene glycol); ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

The term "peptide," as used herein, refers to any compound produced by amide formation between a carboxyl group of one amino acid and an amino group of another group. The term "oligopeptide," as used herein, refers to peptides with fewer than about 10 to 20 residues, i.e., amino acid monomeric units. As used herein, the term "polypeptide" refers to peptides with more than 10 to 20 residues. The term "protein," as used herein, refers to polypeptides of specific sequence of more than about 50 residues, e.g., peptides, enzymes, glycoproteins, hormones, receptors, antigens, antibodies, growth factors, etc.

A peptide can be naturally occurring, recombinantly produced, or synthetically produced. Thus, the terms "peptide," "oligopeptide," "polypeptide" include peptides in which the conventional backbone has been replaced with non-naturally occurring or synthetic backbones, and peptides in which one or more of the conventional amino acids have been replaced with one or more non-naturally occurring or synthetic amino acids. A peptide may be made by cleavage or proteolysis (e.g., protease digestion) of a polypeptide or protein. A peptide that is produced by cleavage or proteolysis typically comprises from 2 to 50 amino acids, but other lengths are also possible.

The term "peptide mixture", as used herein, refers typically to a complex mixture of peptides, for example, obtained as a result of the cleavage of a sample comprising proteins.

The term "purified" or "to purify", as used herein, refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule result in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

The term "sample", as used herein, refers to a material or mixture of materials, typically, although not necessarily, in liquid form, containing one or more analytes of interest. For example, a sample may include a mixture of biomolecules, e.g., peptides.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in Protective Groups in Organic Synthesis, Third Ed. Greene, T. W. and Wuts, P. G., Eds., John Wiley & Sons, New York: 1999.

It will be appreciated that the compounds, as described herein, may be substituted with any number of substituents or functional moieties.

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

DETAILED DESCRIPTION

The invention provides novel IMS-MS tags and shifting agents, and compositions and preparation methods thereof, which can substantially enhance separation of multiple components in complex samples and facilitate quantitative and higher-order multiplexed analyses (hyperplexing).

For example, in some embodiments of the present invention, multiple samples are provided that may contain a same analyte. Each of the multiple samples is labeled with a distinct tag. The tags comprise a linker group of various masses and a normalizing group of various masses, where the combined mass of the linker group and the normalizing group in each tag is a constant for all the tags. Thus, the mass of the normalizing group in each tag is characteristic of the tag as well as the sample labeled with the particular tag. The labeled analyte (tag-analyte) forms a ring structure, which changes its collisional cross section compared to the unlabeled analyte and determines its mobility in IMS. The multiple labeled samples are mixed, and the mixture is subject to IMS-MS. IMS separates the compounds in the mixture based on mobility, and MS further separates the compounds based on their mass/charge ratios. To quantitate the same analyte from different samples, fragmentation is performed to release the normalizing group from the compound, and the amount of the normalizing group is an indication of the amount of the analyte in the particular sample each normalizing group is associated with. To facilitate an even higher level of separation, the sample mixture can be separated using any convenient method prior to IMS-MS, such as by liquid chromatography (LC), electrophoresis, or the like.

The invention overcomes a number of inadequacies and deficiencies of conventional IMS-MS shifting agents. These unique tags and shifting agents enable significant additional separations of analytes while simultaneously providing multiplexed quantitation of the same analytes from different samples.

Generally speaking, there are two categories of quantification strategies: label-free and label-based. In label-based quantification, chemical tags are added (e.g., coupled using an amine-reactive or a thiol-reactive chemistry) to analytes (e.g., via the amine or thiol groups of proteins or peptides) so they can be differentiated in mass spectra. In specific embodiments, the tag is a compound that includes a peptide reactive group selected from the group consisting of a maleimide moiety, a bromoacetamide moiety, a pyridyldithio moiety, an iodoacetamide moiety, a methanethiosulfonate moiety, an isothiocyanate moiety, and an N-hydroxysuccinimide ester moiety. Label-based quantification has an inherent advantage, i.e., capable of distinguishing in one analysis the same analyte from different samples because they bear different labels, therefore facilitating multiplexing for greatly increased throughput. Two main types of labels are used: non-isobaric and isobaric tags. Isobaric tags traditionally are composed of light and heavy isotopes that balance to yield the same mass shift (i.e., a change in mass/charge ratio due to the addition of the label) under non-fragmenting conditions, but can be fragmented to produce reporter tags that provide quantification. Non-isobaric tags have different masses and impart a differentiated mass shift so that species can be distinguished and quantified under non-fragmenting mass spectrometric conditions. One disadvantage is the addition of peaks results in denser mass spectra. As a result, non-isobaric tags are typically limited to two or at most three tags.

Crown ethers have been studied as IMS-MS shift agents before. (Bohrer, et al. 2011 *Anal. Chem.* 83(13): 5377-5385.) They have been investigated as agents to modify collisional cross sections of peptides as they drift through the drift tube prior to entering the mass spectrometer. The crown ethers, however, have only been employed to form non-covalent inter-molecular complexes with the analytes. Inter-molecular complexes between peptides and crown ethers migrate in IMS according to collisional cross section and charge states induced by the complexation, which is a result of the on/off kinetics of the interaction of the peptide with the crown ether. (Hilderbrand, et al. 2006 *Anal. Chem.* 18(19): 6792-6800.) Although this strategy has provided some added resolution, it is not applicable to multiplex samples, does not enable quantitation, and does not provide adequate increase in resolution.

The present invention is based on a unique strategy distinctive from all existing methodologies for IMS separation and multiplexed quantitation. In some aspects of the present invention, the crown ethers are covalently attached to the analytes, which substantially improves the drift time differentiation of peptides in IMS.

Figure 3:
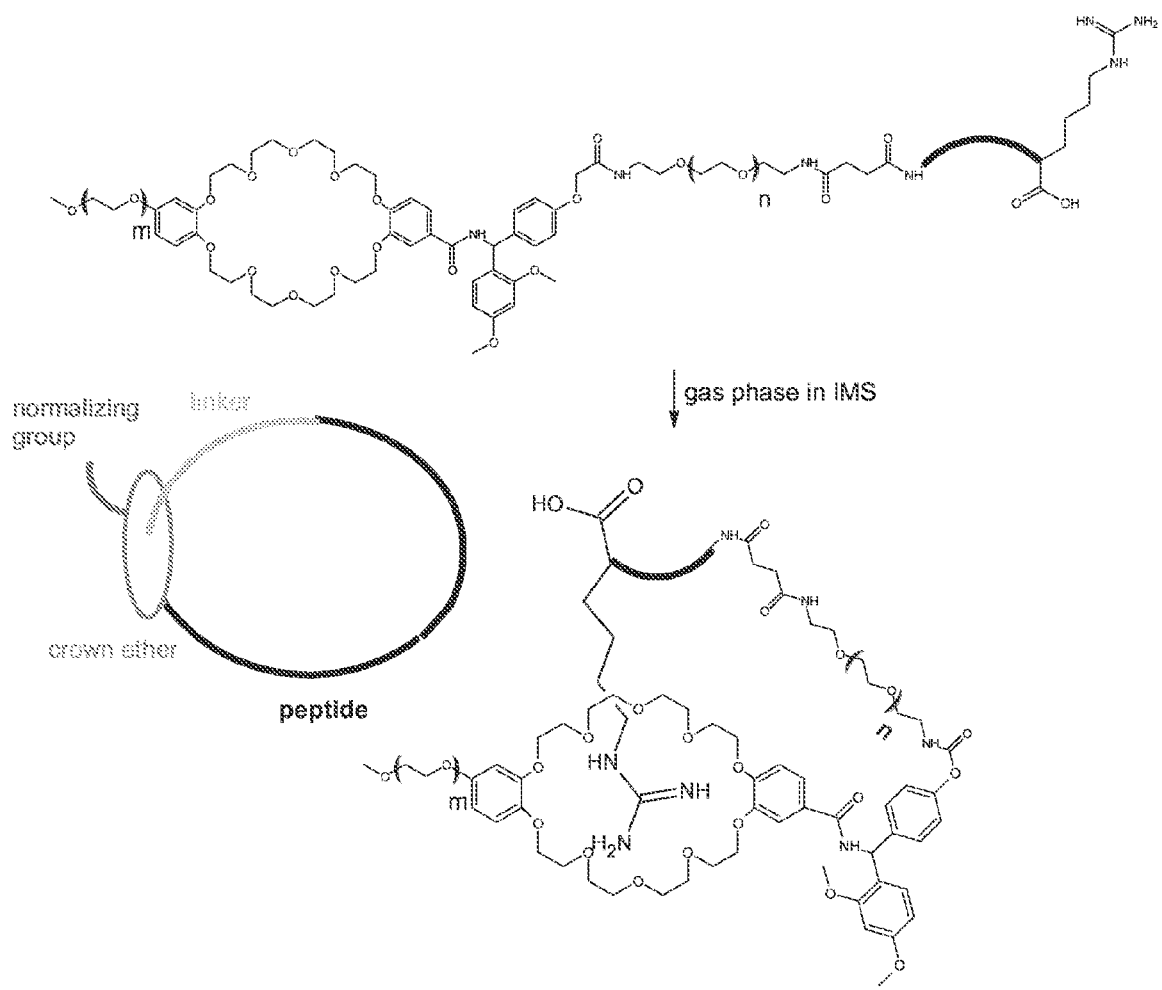
FIG. 3 shows a schematic illustration of an exemplary embodiment of an IMS-MS conjugate and the formation of an intra-molecular complex.

Separation in IMS is influenced by the size of the ring formed intra-molecularly between the crown ether and the analyte (e.g., a terminal guanidinium group at the C-terminus of a peptide fragment complexing to the crown ether) (FIG. 3). Such an intra-molecular complex modifies the collisional cross section depending on the size of the ring (tunable by the number of monomer units in the linker). Thus, one aspect of this invention provides methods of covalently linking an analyte to a crown ether or a crown ether-containing compound, whereby the crown ether and the analyte interact with each other to form an intra-molecular complex, and subjecting the intra-molecular complex to IMS. Non-cyclic versions of crown ethers or crown ether-like compounds such as cryptands, as described in more detail below, can also be used in the same manner as a crown ether.

Therefore, the invention provides compounds useful as tags that contain an intra-molecular binding moiety. The intra-molecular binding moiety is capable of binding an analyte of interest, so when the analyte is labeled with the tag, an intra-molecular complex is formed through the intra-molecular binding moiety and the analyte. The intra-molecular binding moiety can be, by way of example, crown ether, aza-crown ether, sulfur-containing crown ether, cryptands, calixarene, cylophane, cyclodextrin, and ether-based podand. In this disclosure, crown ether is typically used to indicate an intra-molecular binding moiety, although other intra-molecular binding moieties can be used in its place.

Quantitation of comparative samples can be achieved by a non-isobaric method. A plurality of tags can be prepared which all contain an intra-molecular binding moiety, such as a crown ether, bonded to a group of varying masses. For example, each tag may differ only by the number of repeats of a structural unit such as an ethylene group or ethylene oxide group. Any convenient structural units that can serve this purpose may be utilized. Each sample can be labeled with a different tag to facilitate a multiplex analysis. The intra-molecular complexes enhance resolution in IMS, while the tag of varying masses can be used in MS analysis to identify which original sample an analyte comes from.

Quantitation of comparative samples can also be achieved with iso-baric tags, for example, by having a linker group and a normalizing group in the tag. The linker group and the normalizing group typically have a repeatable monomer unit, which monomer may or may not be the same between the linker group and the normalizing group. However, the total mass of each tag is a constant. In some isobaric embodiments, the monomer units are the same, and the number of monomer units in the linker (usually coupling the analyte to the crown ether) and the number of monomer units in the normalizing group (usually hanging off the other side of the crown ether) add up to the same constant for the different samples. (See, FIG. 1, where n+m=x, wherein each of n, m, and x is an integer). A person of ordinary skill would readily appreciate that the linker group and the normalizing group have complimentary roles. For example, in some cases, the group that couples the analyte to the crown ether can be called the normalizing group, in which case the group on the other side of the crown ether would be called the linker. In some cases, all the tags have similar chromatographic properties, especially in reversed phase conditions, so that the same analytes elute together even if they are coupled to different tags.

Upon activation (e.g., via lower energy collision-induced dissociation (CID) or in-source CID), the crown ether breaks off and allows the specific sample to be identified by the number of monomers present in the normalizing group, even though the peptides from various samples with the conjugates are isobaric in full scan MS.

Furthermore, the present invention allows for hyperplexing of complex samples. By incorporating heavy atoms into the monomer units in the linker units and normalizing units (e.g., $^2$H, $^{13}$C, $^{18}$O, for the monomers shown), a combination of the heavy isotope labeled species and varying monomer units allow for a large number of samples to be analyzed with very similar chromatographic behavior (e.g., having either isobaric masses or offset masses based on the heavy isotope). For example, the isotopes can be incorporated through synthetically made ethylene glycol units, which can have O, N or H isotopes. Lighter isotopes, or a mix of lighter and heavier isotopes, can be similarly used.

Thus, in some embodiments, IMS offers an additional dimension of separation after chromatography in the reversed phase, in which the tags behave similarly if not identically, and finally isobaric MS (or offset in the case of heavy/light isotopes) is performed with varying reporter masses in MS/MS for quantitation. Sequencing of the peptides can be achieved by a variety of dissociation strategies (e.g., CID, ETD, ECD) in the mass spectrometer.

Figure 4:
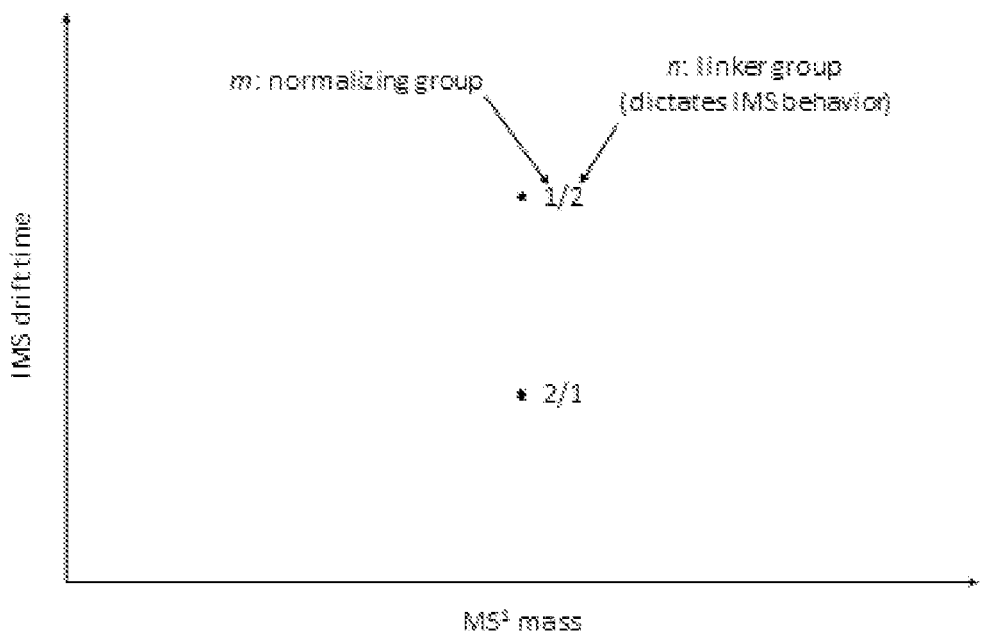
FIG. 4 shows a schematic illustration of an exemplary embodiment for quantitation of an analyte using IMS-only tags.
Figure 5:
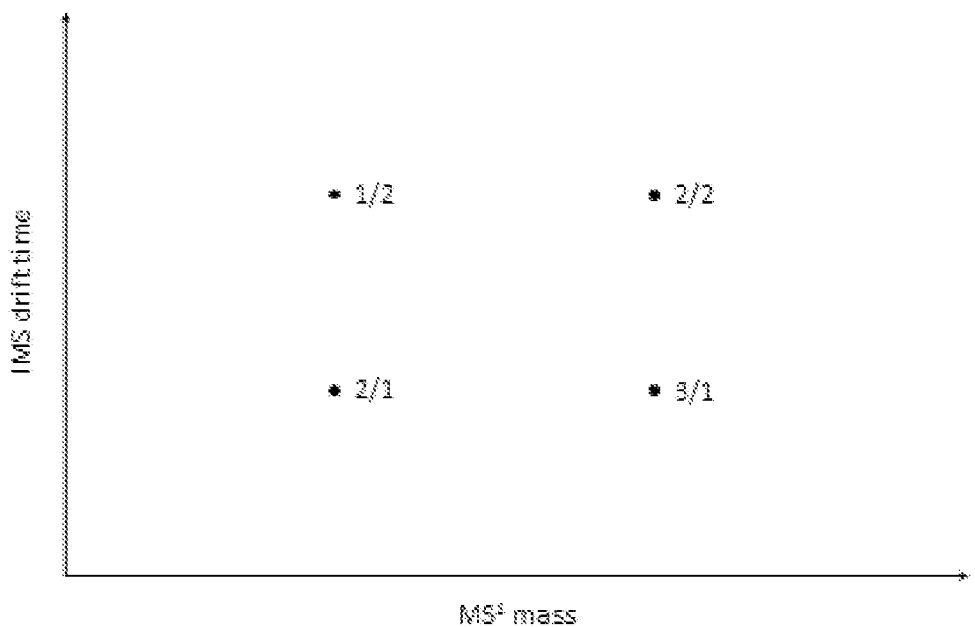
FIG. 5 shows a schematic illustration of an exemplary embodiment for quantitation of an analyte using IMS+MS$^1$ tags.
Figure 6:
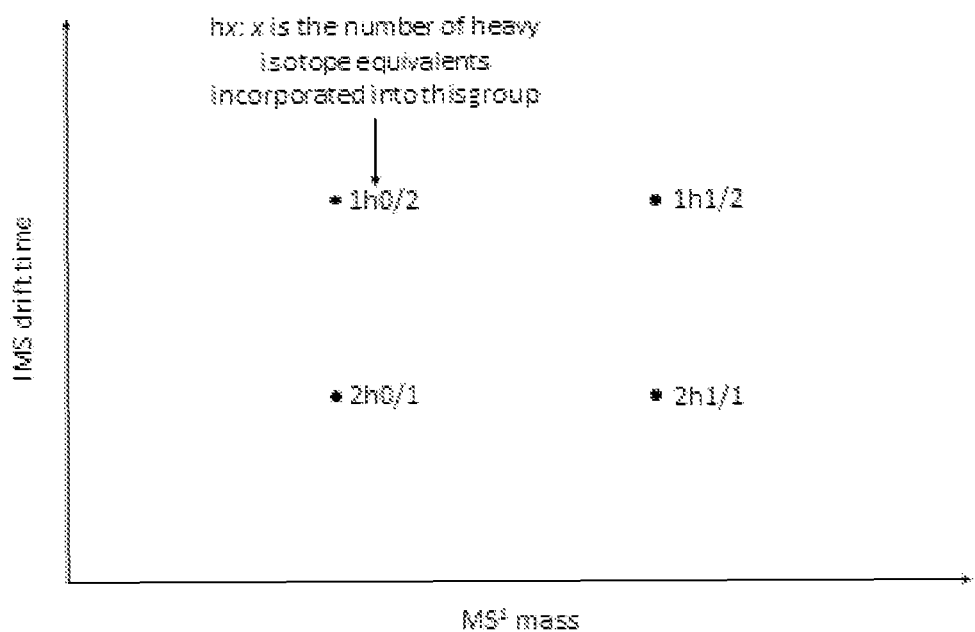
FIG. 6 shows a schematic illustration of an exemplary embodiment for quantitation of an analyte using IMS+MS$^1$ heavy isotope tags.
Figure 7:
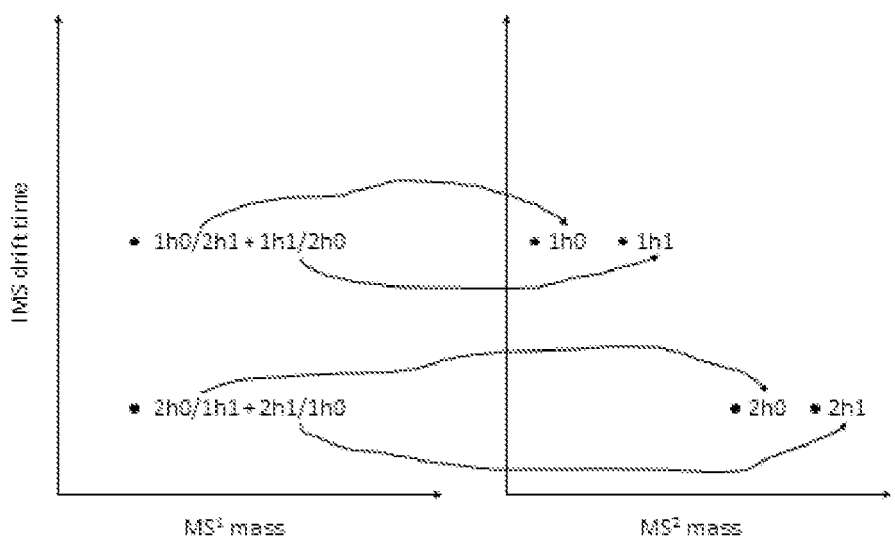
FIG. 7 shows a schematic illustration of an exemplary embodiment for quantitation of an analyte using IMS+MS$^2$ tags.
Figure 8:
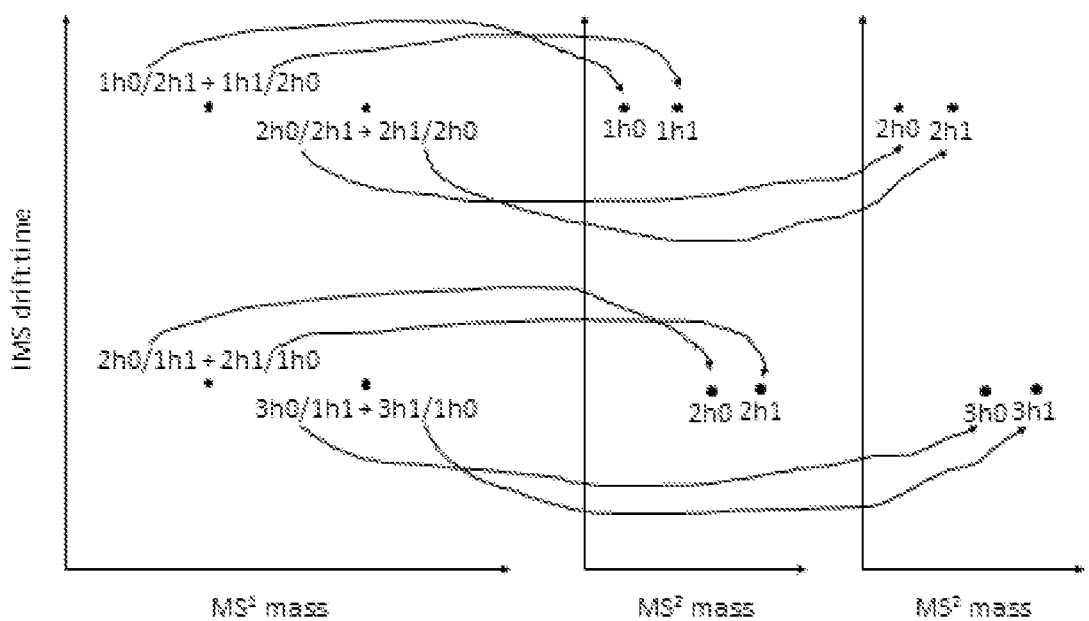
FIG. 8 shows a schematic illustration of an exemplary embodiment for quantitation of an analyte using IMS+MS$^1$+MS$^2$ tags.

Quantitation can be achieved in one of four ways. In FIG. 4, two or more samples comprising the same analyte are labeled with versions of the tag that have the same mass but different numbers of repeating units in the normalizing and linker groups. These labeled analytes will have different IMS drift times and therefore can be quantitated separately. In FIG. 5, four or more samples are labeled with versions of the tag that differ in both mass and number of repeating units in the normalizing and linker groups. Alternatively, as shown in FIG. 6, heavy isotopes can be incorporated into the linker group to achieve the same effect. These labeled analytes will differ by MS mass and/or IMS drift time and can be quantitated separately. In FIG. 7, four or more samples that are labeled with versions of the tag that are the same in mass but have heavy isotopes incorporated into either the normalizing or linker groups. When subjected to MS/MS, the normalizing group will dissociate and appear as a reporter ion in the mass spectrum, indicating the amount of the species present from which it originated. FIG. 8 combines the ideas of FIG. 5 and FIG. 7. Eight or more samples can be quantitated simultaneously due to each having a unique combination of IMS drift time, MS mass, and MS/MS reporter mass. Therefore, each can be quantitated separately. All four of these strategies add IMS as an additional dimension of separation which increases multiplexing capability by at least a factor of two. This can be achieved without adding peaks to MS spectra, which increases spectral complexity and results in reduced identifications.

In some cases, for peptide analysis, the following chemistry can be used for labeling. Lysine residues can be selectively converted to homoarginine residues. (See, e.g., Hilderbrand, et al. 2006 *Anal. Chem.* 18(19): 6792-6800.) In some cases, this causes all of the C-terminal amino acids of peptides from a tryptic digest, e.g., arginines and lysines (converted to homoarginine) to contain a guanidinium group (FIG. 1). Any convenient crown ethers may be utilized to bind guanidinium moieties through hydrogen bonding or electrostatics and hydrogen bonding, causing intra-molecular complexation to form rings. (see, e.g., Julian, et al. 2004 *J. Am. Soc. Mass Spectrom.* 15, 616-624; Julian, et al. 2002 *Int. J Mass Spectrom.* 220: 87-96.) (FIG. 3) It is advantageous that guanidinium moieties are known to ionize better than primary amines (i.e., arginine ionizes better than lysine). The conversion from lysine to homoarginine is optional, especially for peptide samples that only have arginines at the terminals.

In some embodiments, the tag is a compound includes A, Q, X and L, wherein A is a group comprising a first structural unit; Q is a cyclic group comprising three or more groups selected from oxo-hydrocarbon groups and amino-hydrocarbon groups; X is a cleavable group; and L is a group comprising a second structural unit. Any convenient configurations of A, Q, X and L may be utilized in the subject compounds. In some instances, A, Q, X and L are arranged sequentially in any convenient order. In some instances, a branched configuration of A, Q, X and L is utilized. It should be noted that as long as X is between A and L, the compound will work in the subject methods. In some cases, Q may be connected to a sequence of A-X-L or L-X-A at any convenient location, e.g. at A, at X or at L. In certain cases, Q is connected via A. In certain cases, Q is connected via X. In certain cases, Q is connected via L.

In one aspect, the invention generally relates to a compound having the formula of

wherein
A is a group comprising a first structural unit;
Q is a cyclic group comprising three or more groups selected from oxo-hydrocarbon groups and amino-hydrocarbon groups;
X is a cleavable group; and
L is a group comprising a second structural unit., A-Q-X-L, A-X-Q-L, Q-A-X-L, etc, are all contemplated in this disclosure. When X is cleaved to generate a reporter tag, the reporter can be, for example, A-Q or L-T (from A-Q-X-L) or A or Q-L-T (from A-X-Q-L), etc. to serve the same purpose of a reporter tag, because they contain a group of varying mass.

In some embodiments, the compound is of one of the following formulae:

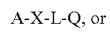

wherein A, Q, X and L are as defined above.

In certain embodiments, the first and the second structural units are selected from the group consisting of alkylene oxide and alkylene diamine structural units.

In certain embodiments, the first and the second structural units are selected from the group consisting of ethylene-oxide and ethylene diamine structural units. In certain embodiments, the first and second structural units have the same mass. In certain embodiments, the first and second structural units have the same m/z.

In certain embodiments, Q is a crown ether and the first and the second structural units are identical. In certain embodiments, the crown ether is selected from dibenzo-30-crown-10,30-crown-10,27-crown-9, dibenzo-27-crown-9,24-crown-8, dibenzo-24-crown-8,21-crown-7, dibenzo-21-crown-7, dibenzo-18-crown-6,18-crown-6,15-crown-5,12-crown-4, diaza-18-crown-6, and derivatives thereof.

In certain embodiments, Q includes a crown ether. In certain embodiments, Q includes an aza-crown ethers. In certain embodiments, Q includes a sulfur-containing crown ether. In certain embodiments, Q includes a cryptand. In certain embodiments, Q includes a calixarene. In certain embodiments, Q includes a cylophane. In certain embodiments, Q includes a cyclodextrin.

In some cases, the compound may include at any convenient position a functional group capable of coupling with an analyte of interest. In some cases, the analyte is a peptide or protein and the functional group is a peptide linking group. As used herein, the term "peptide reactive group" refers to a group that is capable of reacting directly either spontaneously or after activation through contact with a stimulus, e.g., light, with an accessible terminal or sidechain functional group of a peptide or protein to produce a covalent linkage to the protein. The peptide reactive group is capable of reaction with one or more functional groups of a protein of interest, such as an N-terminal amino group or a sidechain group of a Lys, Cys, Ser, Thr, Tyr or H is amino acid residue of the protein, i.e., the protein linking group may be amino-reactive, thiol-reactive, hydroxyl-reactive, or imidazolyl-reactive. Exemplary peptide reactive groups include active esters (e.g., an amino-reactive NHS ester), and thiol-reactive maleimide or iodoacetamide groups. Further exemplary peptide reactive groups and methods of using the same are described in Hermanson, "Bioconjugate Techniques" 2nd Edition, Academic Press, 2008.

Figure 2:
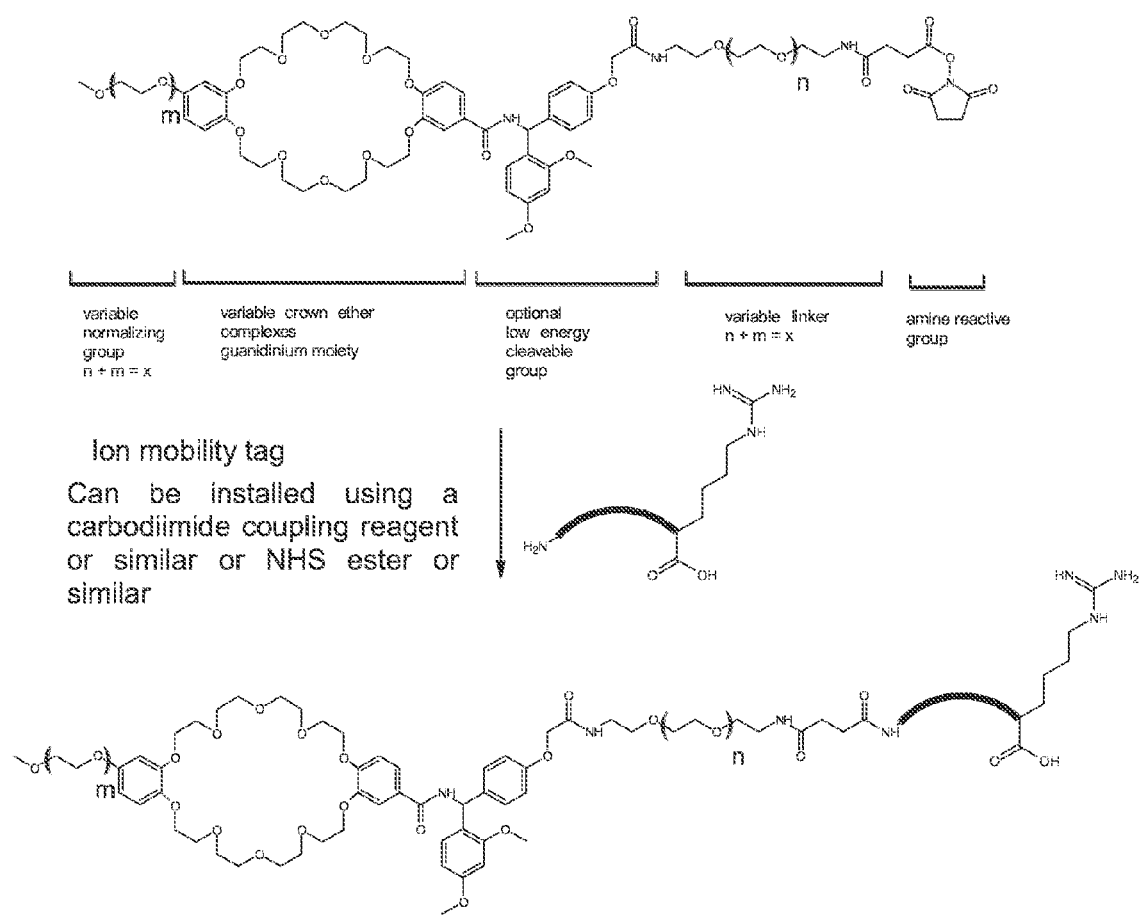
FIG. 2 shows a schematic illustration of an exemplary embodiment of the IMS-MS tag compound and its use in coupling with an analyte of interest.

In specific embodiments, the tag is a compound that includes a peptide reactive group selected from the group consisting of a maleimide moiety, a bromoacetamide moiety, a pyridyldithio moiety, an iodoacetamide moiety, a methanethiosulfonate moiety, an isothiocyanate moiety, and an N-hydroxysuccinimide ester moiety. In some embodiments, the compound includes an amine reactive moiety. In some embodiments, the amine reactive moiety couples the N-terminal of a peptide analyte of interest. (FIG. 2)

In some embodiments, A includes a functional group capable of coupling with an analyte of interest. In certain embodiments, A includes a peptide reactive group. In certain cases, A includes an amino-reactive NHS ester.

In some embodiments, L includes a functional group capable of coupling with an analyte of interest. In certain embodiments, L includes a peptide reactive group. In certain cases, L includes an amino-reactive NHS ester.

In some embodiments, X includes a functional group capable of coupling with an analyte of interest. In certain embodiments, X includes a peptide reactive group. In certain cases, X includes an amino-reactive NHS ester.

In some embodiments, Q includes a functional group capable of coupling with an analyte of interest. In certain embodiments, Q includes a peptide reactive group. In certain cases, Q includes an amino-reactive NHS ester.

In another aspect, the invention generally relates to a compound having the formula of

A-Q-X-L-T    (II)

wherein
A is a normalizing group comprising a structural unit;
Q is a cyclic group comprising three or more groups selected from oxo-hydrocarbon groups and amino-hydrocarbon groups;
X is a cleavable group;
L is a linker comprising the structural unit; and
T is an oligomer comprising a group capable of forming an intra-molecular complex with Q.

In certain embodiments, the oxo-hydrocarbon is an alkylene oxide and the amino-hydrocarbon is an alkylene diamine. In certain embodiments, the cyclic group comprises three or more ethylene-oxide units. In certain embodiments, the cyclic group comprises three or more ethylene-diamine units.

Any of the tag compounds described herein may be coupled with an analyte of interest. In some embodiments, the analyte of interest is an oligomer T. T may be attached to the tag compound at any convenient position. In some embodiments, T is attached to A, in some embodiments, T is attached to L. In certain embodiments, T is attached to X. In certain embodiments, T is attached to Q. In some embodiments, the compound is of one of the following formulae:

Q-A-X-L-T

A-Q-X-L-T

A-X-Q-L-T

A-X-L(T)-Q, or

A-X(-Q)-L-T wherein A, Q, X, L and T are as defined above.

In some embodiments, the compound is of one of the following formulae:

Q-A(T)-X-L

T-A-Q-X-L

T-A-X-Q-L

T-A-X-L-Q, or

T-A-X(-Q)-L wherein A, Q, X, L and T are as defined above.

In some embodiments, the compound is of one of the following formulae:

Q-A-X(T)-L

A-Q-X(T)-L

A-X(T)-Q-L

A-X(T)-L-Q, or

A-X(T)(Q)-L wherein A, Q, X, L and T are as defined above.

In some embodiments, the compound is of one of the following formulae:

Q(T)-A-X-L

A-Q(T)-X-L

A-X-Q(T)-L

A-X-L-Q-T, or

A-X(-Q-T)-L wherein A, Q, X, L and T are as defined above.

In certain preferred embodiments, Q is a crown ether moiety and T is a peptide including a terminal guanidinium moiety.

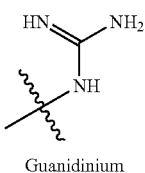 [SMILES: *NC(=N)N]

Guanidinium

In certain embodiments, A includes an ethylene-oxide structural unit; L includes an ethylene-oxide structural unit; and X includes a cleavable moiety having a low dissociation energy.

In certain embodiments, A includes an ethylene diamine structural unit; L includes an ethylene diamine structural unit; and X includes a cleavable moiety having a low dissociation energy.

The crown ether may be any suitable crown ether, for example, selected from dibenzo-30-crown-10,30-crown-10, 27-crown-9, dibenzo-27-crown-9,24-crown-8, dibenzo-24-crown-8,21-crown-7, dibenzo-21-crown-7, dibenzo-18-crown-6,18-crown-6,15-crown-5,12-crown-4, diaza-18-crown-6, and derivatives thereof, such as aza, diaza, triaza, tetraaza, etc., derivatives thereof.

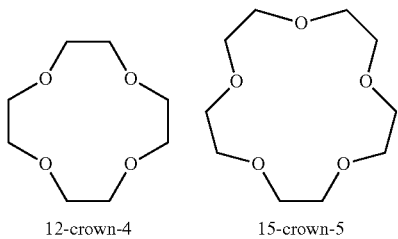

12-crown-4    15-crown-5

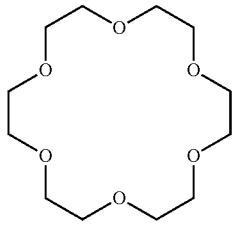

18-crown-6

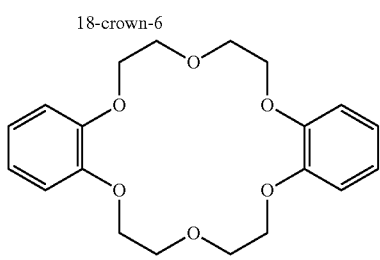

dibenzo-18-crown-6

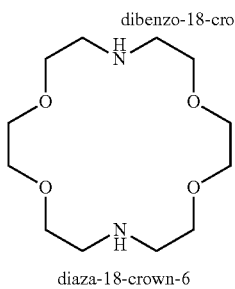

diaza-18-crown-6

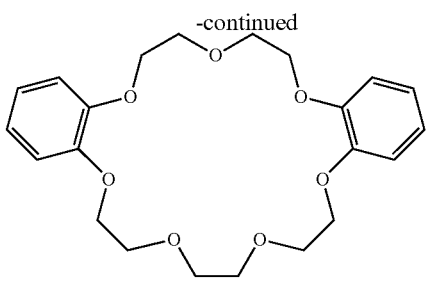

dibenzo-21-crown-7

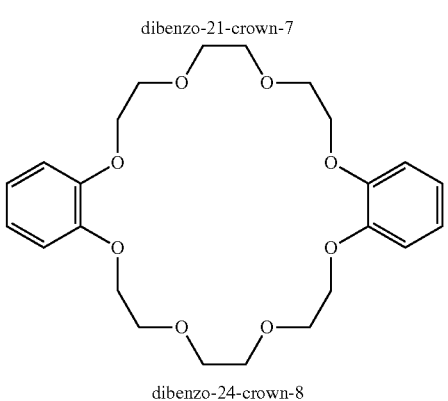

dibenzo-24-crown-8

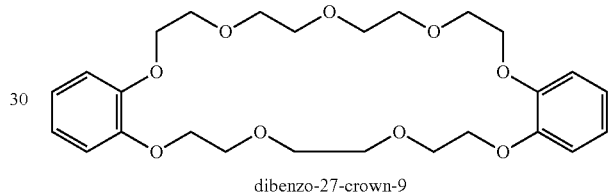

dibenzo-27-crown-9

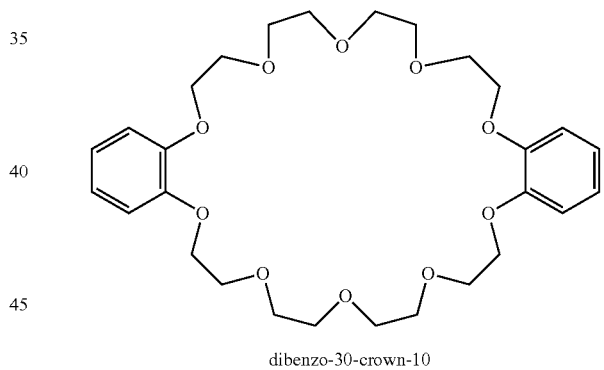

dibenzo-30-crown-10

It is noted that acyclic crown ether analogs may also be used to serve as ligands. Examples of such crown ether analogs include oligo- or poly-ethylene glycols, such as

$R_1OCH_2(CH_2OCH_2)_nCH_2OR_2$ wherein each $R_1$ and $R_2$ is selected from H or an alkyl group (e.g., methyl, ethyl), n is from about 2 to about 20 (e.g., from about 2 to about 15, from about 2 to about 10, from about 2 to about 8, from about 2 to about 5). Derivatives of oligo- and poly-ethylene glycols may also be suitable. (Gokel, et al. 1983 *J. Org. Chem.* 48:2837-2842; Kron, et al. 1990 *Russian Chem. Rev.* 59 (3) 283.) Complexing moieties of interest include, but are not limited to, aza-crown ethers, sulfur-containing crown ethers, cryptands (Bochenska et al., 1993, *J Incl Phenom Macrocycl Chem*, 16(1):63-68), calixarenes (Casnati et al., 1992, *Isr. J. Chem.*, 32:79-87), cylophanes (Ariga et al., 2003, *Supramolecular Chemistry*, 15(2):87-94), and cyclodextrins (Kataky et al., 1994, *J. Chem. Soc., Perkin*

Trans. 2, 12:2381-2382) which may be utilized to complex with guanidinium moieties and may be used as the crown ether moiety. Such crown ether analogs may be used in place of the crown ethers described, or the crown ethers may be omitted, and the crown ether analogs may comprise the linker (L) and the normalizing group (A). T may be any suitable peptide, for example, comprising from about 1 to about 30 (e.g., from about 2 to about 30, from about 2 to about 20, from about 2 to about 10, from about 1 to about 10, from about 1 to about 8, from about 1 to about 5, e.g., 1, 2, 3, 4, 5) amino acid units. For example, the peptides may be dimer, trimer, tetramer of amino acids.

In certain embodiments, Q includes a crown ether. In certain embodiments, Q includes an aza-crown ethers. In certain embodiments, Q includes a sulfur-containing crown ether. In certain embodiments, Q includes a cryptand. In certain embodiments, Q includes a calixarene. In certain embodiments, Q includes a cylophane. In certain embodiments, Q includes a cyclodextrin.

The normalizing group may be any suitable group. The number of structural units in the normalizing group is referred to as "m" in m+n=x, wherein x is an integer equals to or greater than 1; and n and m are independently integers including 0, 1, 2, 3, . . . (see, e.g., FIG. 2). For instance, to perform 4-plex, one would have m=3 and n=0, m=2 and n=1, m=1 and n=2, and m=0 and n=3.

The linker group may be any suitable group. The number of structural units in the linker group is referred to as "n" in m+n=x (see FIG. 2). For instance, to perform 4-plex, one would have m=3 and n=0, m=2 and n=1, m=1 and n=2, and m=0 and n=3

Each of A and L may comprise any suitable number of repeating units, for example, from about 0 to about 20 (e.g., from about 1 to about 20, from about 1 to about 15, from about 1 to about 10, from about 1 to about 8, from about 1 to about 5, e.g., 0, 1, 2, 3, 4, 5) units of repeating units (e.g., ethyleneoxide, ethylene diamine).

Any suitable cleavable moiety may be employed, including, but not limited to, cleavable moieties that comprise a phosphonium (Woo et al., 2009, *Rapid Commun Mass Spectrom.* (12):1849-55), sulfonium (Lu et al., 2008, *Anal Chem.*, 80(23):9279-87), and/or an ammonium (Clifford-Nunn et al., 2012, *J Am Soc Mass Spectrom.* 23(2): 201-212) group. In certain embodiments, the cleavable moiety is

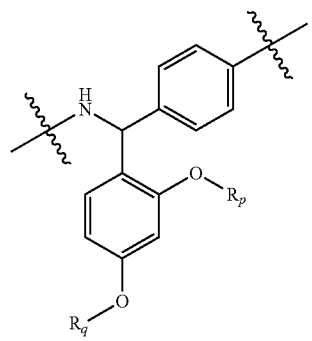

wherein each of $R_p$ and $R_q$ independently is an alkyl group

In yet another aspect, the invention generally relates to a method for analyzing peptides, comprising:

reacting a sample of peptides with one or more compounds having the formula (I) thereby forming one or more compounds of the formula (II):

A-Q-X-L or A-X-Q-L         (I)

A-Q-X-L-T or A-X-Q-L-T         (II)

wherein
A is a normalizing group comprising a structural unit;
Q is a cyclic group comprising three or more ethylene-oxide units;
X is a cleavable group;
L is a linker comprising the structural unit; and
T is a peptide comprising terminal guanidinium moiety, wherein the guanidinium moiety is capable of forming intramolecular complex with Q;

separating the formed compounds of formula (I) by ion mobility; and causing cleavage of the cleavable group and dissociation of the compounds of formula (II) forming fragments of formula (III) or A:

A-Q         (III).

In certain embodiments, the method further includes: measuring the fragments of formula (III) by mass spectroscopy to analyze the peptides.

In certain embodiments, the method further includes, prior to reacting the sample with one or more compounds having the formula (I), pre-treating the sample to be analyzed to chemically introduce a terminal guanidinium moiety into each peptide component in the sample not already having a guanidinium moiety.

Any suitable dissociation method for causing cleavage of the cleavable group may be used, for example, via collision-induced dissociation (CID), electron-capture dissociation (ECD), electron-transfer dissociation (ETD), higher-energy collisional dissociation (HCD, previously higher-energy c-trap dissociation), or pulsed-Q dissociation (PQD).

CID, or collisionally activated dissociation (CAD), is a mechanism by which to fragment molecular ions in the gas phase. (Wells, et al. 2005 *Meth. Enzymol.* 402:148-85; Sleno, et al. 2004 *J. Mass Spectrom.* 39 (10):1091-112.) The molecular ions are typically accelerated by electrical potential to high kinetic energy and then allowed to collide with neutral molecules (e.g., helium, nitrogen or argon). In the collision some of the kinetic energy is converted into internal energy that results in bond breakage and the fragmentation of the molecular ion into smaller fragments. These fragment ions can then be analyzed by a mass spectrometer.

ECD is another method of fragmenting gas phase ions for tandem mass spectrometric analysis (structural elucidation). ECD involves the direct introduction of low energy electrons to trapped gas phase ions. (Zubarev, et al. 1998 *J. Am. Chem. Soc.* 120, 13:3265-66; McLafferty, et al. 2001 *J. Am. Soc. Mass Spectrom.* 12 (3): 245.)

ETD is yet another method of fragmenting ions in a mass spectrometer. Similar to ECD, ETD induces fragmentation of cations (e.g. peptides or proteins) by transferring electrons to them. (Syka, et al. 2004 *Proc. Natl. Acad. Sci. U.S.A.* 101, 26:9528-33; Mikesh, et al. 2006 *Biochim. Biophys. Acta* 1764, 12:1811-22; U.S. Pat. No. 7,534,622.)

HCD is yet another method of fragmenting ions in a mass spectrometer. It is a form of CID that is performed in orbitrap mass spectrometers. Precursor ions are accelerated by electric potential into a region of relatively high pressure of inert gas which causes them to collide, acquire increased internal energy, and fragment. (Olsen, et al. 2007 *Nat. Methods* 4, 9:709-712.)

PQD is yet another fragmentation mechanism that involves precursor ion activation at high Q, a time delay to allow the precursor to fragment, then a rapid pulse to low Q where all fragmentions are trapped. The product ions are then scanned out of the ion trap and detected.

In yet another aspect, the invention generally relates to a method for separating a compound by ion mobility. The method includes: reacting a sample to be analyzed with a first agent to chemically introduce a first ligand into the compound; reacting the sample to be analyzed with a second agent to chemically introduce a second ligand into the compound, thereby causing the formation of an intra-molecular complex between the first and the second ligands; and separating the intra-molecular complex by ion mobility.

In certain preferred embodiments, the first ligand comprises a guanidinium moiety and the second ligand comprises a cyclic group comprising three or more ethylene-oxide units.

The first ligand may be any suitable ligand, for example, a terminal guanidinium moiety. The second ligand may be any suitable ligand, for example, a crown ether.

In certain preferred embodiments, the compound is a peptide comprising from about 2 to about 30 amino acid units. In certain preferred embodiments, the intra-molecular complex further comprises a linear oligomer comprising from about 2 to about 20 of an ethylene-oxide repeating unit.

A suitable sample may comprise one or more analytes, such as proteins; peptides; carbohydrates; nucleic acids; lipids; small molecules; toxins; drugs or drug-like molecules, or derivatives thereof. For example, a sample may comprise a defined combination of natural and/or chemically synthesized species. In certain embodiments, the composition of a sample may not be fully known.

The sample may be prepared from a cell or group of cells, may be a purified fraction from a cell preparation, may be a purified molecule. The cells may be mammalian cells (e.g., human cells); insect cells; yeast cells; fungal cells; and/or bacterial cells. The cells, for example, may be from multicellular organism (e.g., insects and mammals) derived from specific portions of the organism (e.g., specific tissues, organs, or fluids).

The sample may be prepared from cellular components, such as a nucleus, cytoplasm, plasma cell membrane, nucleolus, mitochondria, vacuoles, subcellular organelles, endoplasmic reticulum and/or Golgi apparatus. The sample may be prepared from cells, tissue samples, and/or organs, such as molecular antigens produced from groups of cells, tissue samples, and/or organs. In certain embodiments, the sample may comprise or be derived from, for example, clinical, industrial, agricultural and environmental samples. For example, sample material often may be of medical, veterinary, environmental, nutritional or industrial significance, and include body fluids, such as blood, serum, plasma, cerebrospinal fluid, synovial fluid, saliva, milk, sputum, lung aspirates, mucus, teardrops, exudates, secretions, urine, and fecal matter; microbial culture fluids; aerosols; crop materials; animal meat (e.g., for human consumption or animal feed); and soils and ground waters.

In certain embodiments, the sample may include molecules in pathogens, viruses, bacteria, yeast, fungi, amoebae and insects; molecules in diseased or non-diseased pest animals such as mice and rats; molecules in diseased and non-diseased domestic animals, such as domestic equines, bovines, porcines, caprines, canines, felines, avians and fish; and molecules in diseased and non-diseased humans.

In certain embodiments, the sample may include biological samples derived from a human or other animal source (e.g., body fluids, such as blood, serum, plasma, cerebrospinal fluid, synovial fluid, saliva, milk, sputum, lung aspirates, mucus, teardrops, exudates, secretions, urine, a biopsy sample, a histology tissue sample, a PAP smear, a mole, a wart, etc.) including samples derived from a bacterial or viral preparation, as well as other samples (e.g., agricultural products, waste or drinking water, milk or other processed foodstuff, air, etc.). In certain embodiments, the sample may comprise preparations from one or more of the following: tissue cells, cells cultured in vitro, recombinant cells, infected cells, cells from laboratory animals, cells from mammal patients, cells from human patients, mesenchemal stem cells, stem cells, immuno-competent cells, adipose cells, fibroblasts, natural-killer cells (NK-cells), monocytes, lymphocytes, lymph node cells, T-cells, B-cells, exudate cells, effusion cells, cancer cells, blood cells, red blood cells, leukocytes, white blood cells, organ cells, skin cells, liver cells, splenocytes, kidney cells, intestinal cells, lung cells, heart cells, or neuronal cells.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

EXAMPLES

Tryptic digested peptides are guanidinylated using O-methylisourea. Briefly, enzymatically digested protein solution is mixed with an equal volume of 0.6 M O-methylisourea, and the pH of these mixtures is adjusted to approximately 10.5 by the addition of 1.6 M $Na_2CO_3$ in distilled water. The total volumes are brought to 100 μL with 50 mM $NH_4HCO_3$, a pH of 10.5 is confirmed with pH paper, and the mixtures immediately incubated for 2 h at 37° C. The guanidinated peptide mixtures are then desalted using ZipTipC18 columns according to the manufacturer's protocol. The N-terminus of each peptide is then reacted with the a 10 mM solution of the NHS-ester containing crown ether derivatizing agent in 50 mM $NaHCO_3$ buffer at pH 8.5 for 1 hour. The derivatized peptides are again desalted using ZipTipC18 columns prior to analysis by LC-MS.

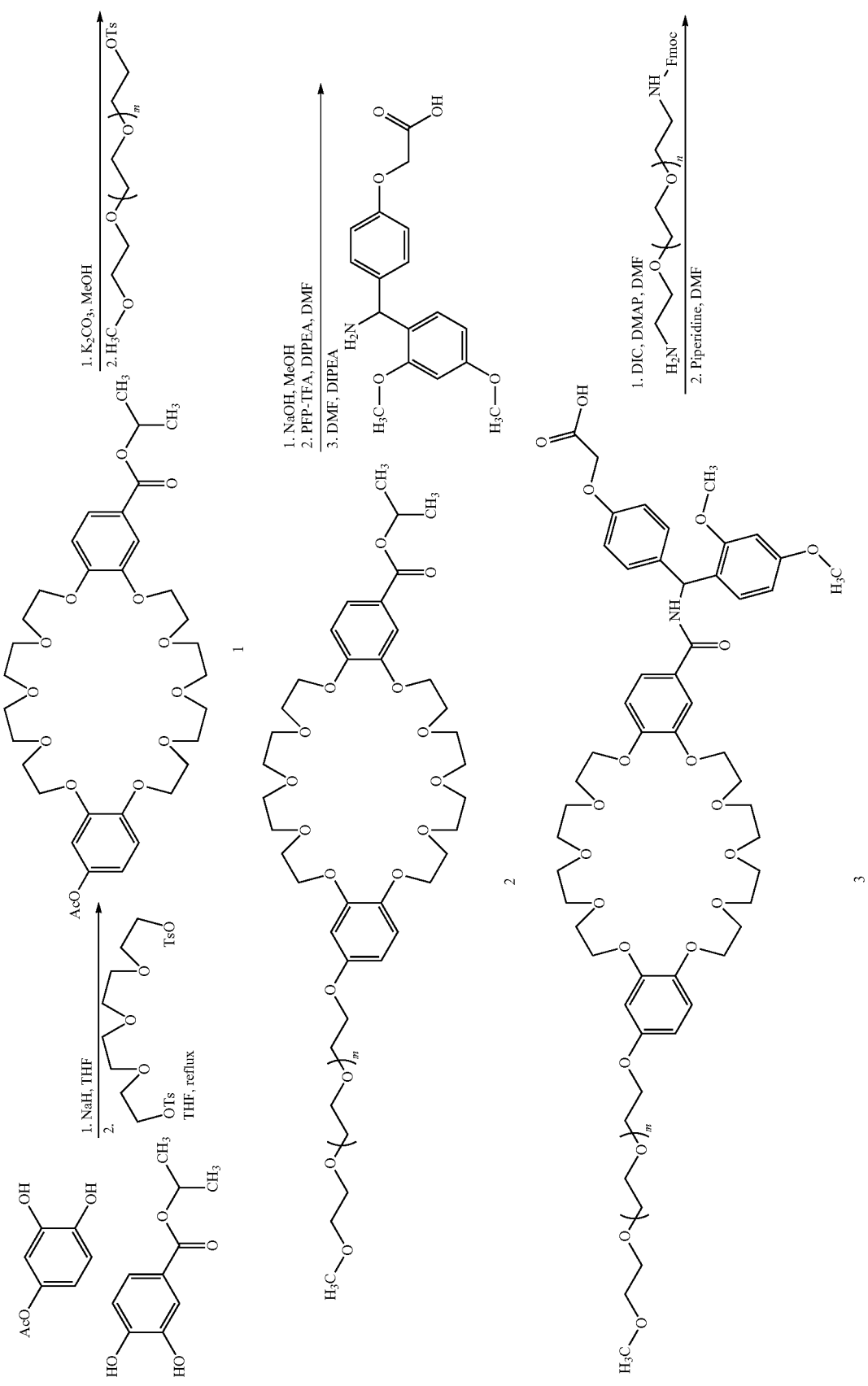

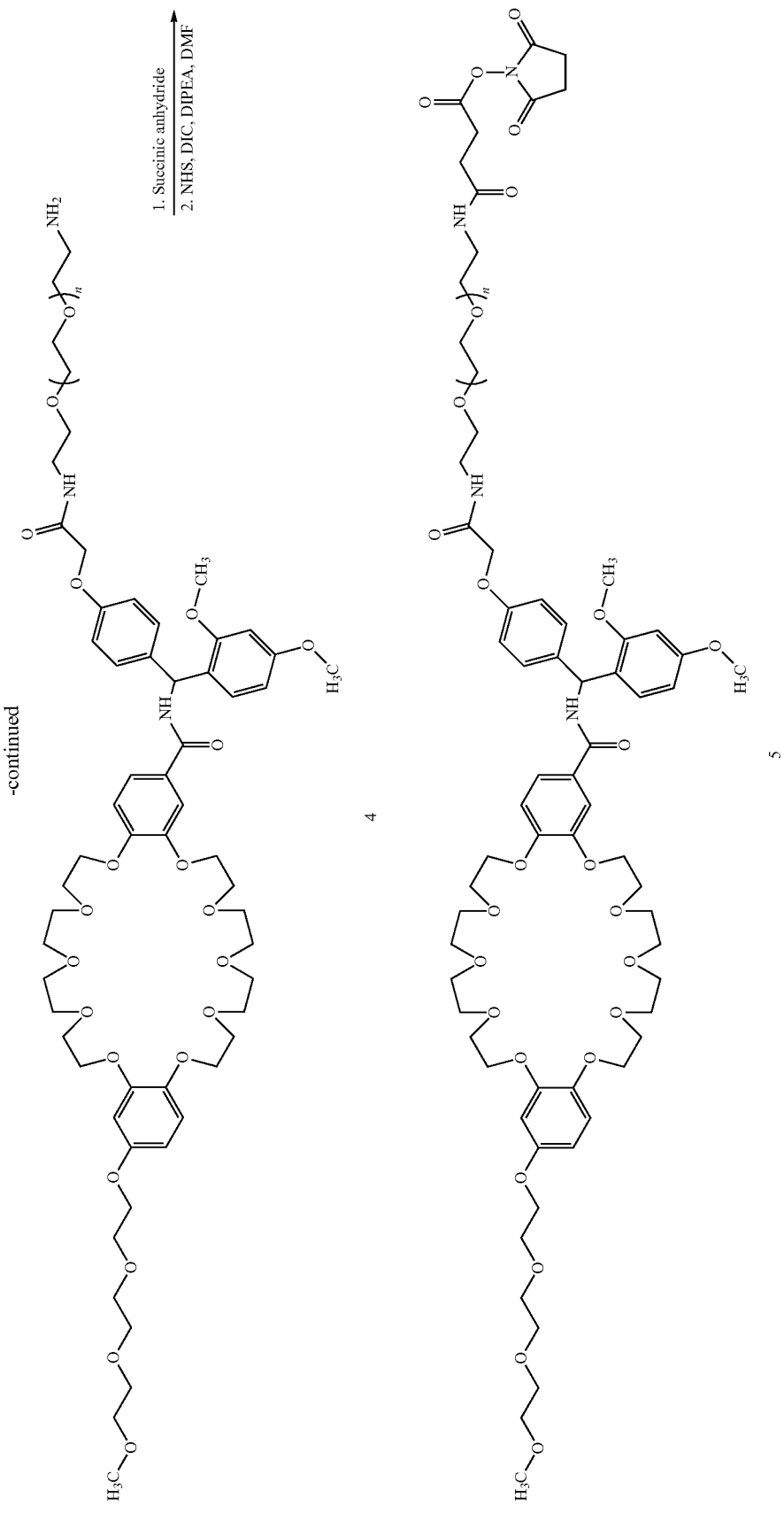

An exemplary synthetic scheme is provided in Scheme 1 and discussed below. Reaction conditions and length may be adjusted according to the scale of reaction and the amounts of reagents used.

Compound 1.

Compound 1 is synthesized according to the procedure of Yan et al. (*Macromolecules*, 2009, 42 (21), pp 8451-8459) except NaH is used as base instead of NaOH.

Compound 2.

To compound 1 in methanol is added the potassium carbonate and stirred at room temperature. Mono-tosylated polyethylene glycol is added and the mixture is refluxed for XX hours and monitored by TLC for completion. The methanol is removed under rotary evaporation and the compound dissolved in EtOAC and washed with 1M HCl, the organic phase separated, and dried over sodium sulfate. The crude material is purified by silica gel column chromatography.

Compound 3.

To compound 2 in methanol is added the sodium hydroxide and stirred at reflux. The methanol is removed under rotary evaporation and the compound dissolved in EtOAC and washed with 1M HCl, the organic phase separated, and dried over sodium sulfate. The crude material is dissolved in anhydrous dimethylformamide, DIPEA added, followed by pentafluorophenyl trifluoroacetate. The reaction is stirred at room temperature under a nitrogen atmosphere and monitored by TLC for completion. An additional equivalent of DIPEA is added followed by 4-[(2,4-Dimethoxyphenyl)-aminomethyl] phenoxyacetic acid and the reaction stirred under a nitrogen atmosphere. The solvent is removed by rotary evaporation and the compound dissolved in EtOAC and washed with 1M HCl, the organic phase separated, and dried over sodium sulfate. The crude material is purified by silica gel column chromatography.

Compound 4.

To compound 3 in anhydrous DMF is added diisopropylcarbodiimide, 4-(dimethylamino)pyridine and mono-Fmoc protected pentaethylene glycol diamine and the reaction stirred under a nitrogen atmosphere. The solvent is removed under rotary evaporation and the compound dissolved in EtOAC and washed with water, the organic phase separated, and dried over sodium sulfate. The crude material is purified by silica gel column chromatography. The purified material is then treated with a 20% v/v solution of piperidine/DMF and stirred. The solvent is removed by rotary evaporation and the material triturated with diethyl ether and collected.

Compound 5.

To compound 4 in anhydrous DMF is added succinic anhydride and the reaction heated to 80° C. The reaction is followed by TLC for completion. To the reaction is then added N-hydroxysuccinimide, diisopropylcarbodiimide, and diisopropylethylamine and stirred under a nitrogen atmosphere. The solvent is removed by rotary evaporation and the crude material is purified by high-pressure liquid chromatography.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature cited herein. The examples contain important additional information, exemplification and guidance that can be adapted to the practice of this invention in its various embodiments and equivalents thereof.

EXEMPLARY EMBODIMENTS

In addition to the embodiments described elsewhere in this disclosure, exemplary embodiments of the present invention include, without being limited to, the following:

1. A compound comprising A, Q, X and L, wherein X is covalently bonded between A and L, such as wherein:
   A is a group comprising a first structural unit;
   Q is a cyclic or non-cyclic group comprising three or more groups selected independently from oxo-hydrocarbon groups and amino-hydrocarbon groups;
   X is a cleavable group; and
   L is a group comprising a second structural unit.
2. The compound of embodiment 1, wherein the first and the second structural units are selected from the group consisting of alkylene oxide and alkylene diamine structural units.
3. The compound of embodiment 1 or 2, wherein the first and the second structural units are selected from the group consisting of a ethylene-oxide structural unit and an ethylene diamine structural unit.
4. The compound of embodiment 1, 2 or 3, wherein Q is a crown ether and the first and the second structural units are identical.
5. The compound of any one of the preceding embodiments, wherein Q is selected from the group consisting of dibenzo-30-crown-10,30-crown-10,27-crown-9, dibenzo-27-crown-9,24-crown-8, dibenzo-24-crown-8,21-crown-7, dibenzo-21-crown-7, dibenzo-18-crown-6,18-crown-6, 15-crown-5,12-crown-4, diaza-18-crown-6, and derivatives thereof.
6. A compound having A, Q, X, L and T covalently bonded sequentially in any order, as long as X is between A and L and T is terminal, such as the formula of $$A\text{-}Q\text{-}X\text{-}L\text{-}T \tag{II}$$

wherein
A is a normalizing group comprising a structural unit;
Q is a cyclic or non-cyclic group comprising three or more groups independently selected from oxo-hydrocarbon groups and amino-hydrocarbon groups;
X is a cleavable group;
L is a linker comprising the structural unit; and
T is an oligomer comprising a group capable of forming an intra-molecular complex with Q.
7. The compound of embodiment 6, wherein the oxo-hydrocarbon is an alkylene oxide and the amino-hydrocarbon is an alkylene diamine.
8. The compound of embodiment 6 or 7, wherein the cyclic group comprises three or more ethylene-oxide units.

9. The compound of embodiment 6 or 7, wherein the cyclic group comprises three or more ethylene-diamine units.
10. The compound of any one of embodiments 6-9, wherein
    Q is a crown ether; and
    T is a peptide comprising a terminal guanidinium moiety.
11. The compound of embodiment 10, wherein
    A comprises an ethylene-oxide structural unit;
    L comprises an ethylene-oxide structural unit; and
    X comprises a cleavable moiety having a low dissociation energy.
12. The compound of embodiment 10, wherein
    A comprises an ethylene diamine structural unit;
    L comprises an ethylene diamine structural unit; and
    X comprises a cleavable moiety having a low dissociation energy.
13. The compound of any one of embodiments 6-12, wherein Q is selected from dibenzo-30-crown-10,30-crown-10,27-crown-9, dibenzo-27-crown-9,24-crown-8, dibenzo-24-crown-8,21-crown-7, dibenzo-21-crown-7, dibenzo-18-crown-6,18-crown-6,15-crown-5,12-crown-4, diaza-18-crown-6, and derivatives thereof.
14. The compound of any one of embodiments 10-13, wherein the peptide comprises from about 1 to about 30 amino acid units.
15. The compound of any one of embodiments 1-14, wherein each of A and L independently comprises from about 1 to about 20 units of the ethylene-oxide repeating unit.
16. The compound of any one of embodiments 1-14, wherein each of A and L comprises from about 1 to about 20 units of the ethylene diamine repeating unit.
17. The compound of any one of the preceding embodiments, wherein the cleavable moiety comprises a phosphonium, a sulfonium or an ammonium group.
18. The compound of any one of the preceding embodiments, wherein the cleavable moiety is

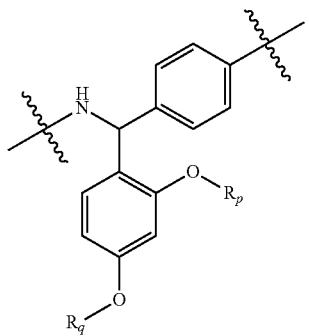

wherein each of $R_p$ and $R_q$ is independently an alkyl group.
19. A method for analyzing one or more peptides, comprising:
    reacting a sample comprising one or more peptides with one or more compounds of embodiment 1 thereby forming one or more compounds of embodiment 6,
    wherein
    A is a normalizing group comprising a structural unit;
    Q is a cyclic or non-cyclic group comprising three or more groups selected independently from oxo-hydrocarbon groups and amino-hydrocarbon groups;
    X is a cleavable group;
    L is a linker comprising the structural unit; and
    T is a peptide comprising terminal guanidinium moiety, wherein the guanidinium moiety is capable of forming intra-molecular complex with Q; and separating the sample by ion mobility spectrometry.
20. The method of embodiment 19, further comprising analyzing the sample by mass spectrometry.
21. The method of embodiment 19 or 20, further comprising:
    cleaving the cleavable group to produce fragments; and
    measuring the fragments by mass spectrometry to analyze the peptides.
22. The method of any one of embodiments 19-21, further comprising, prior to reacting the sample with one or more compounds having the formula (I),
    pre-treating the sample to be analyzed to chemically introduce a terminal guanidinium moiety into each peptide component in the sample not already having a guanidinium moiety.
23. The method of embodiment 21 or 22, wherein causing cleavage of the cleavable group is via collision-induced dissociation (CID), electron-capture dissociation (ECD), electron-transfer dissociation (ETD), higher-energy collisional dissociation (HCD, previously higher-energy c-trap dissociation), or pulsed-Q dissociation (PQD).
24. The method of any one of embodiments 19-23, wherein:
    Q is a crown ether;
    A comprises an ethylene-oxide repeating unit;
    L comprises an ethylene-oxide repeating unit; and
    X comprises a cleavable moiety having a low dissociation energy.
25. The method of any one of embodiments 19-24, wherein the crown ether is selected from dibenzo-30-crown-10,30-crown-10,27-crown-9, dibenzo-27-crown-9,24-crown-8, dibenzo-24-crown-8,21-crown-7, dibenzo-21-crown-7, dibenzo-18-crown-6,18-crown-6,15-crown-5,12-crown-4, diaza-18-crown-6, and derivatives thereof.
26. The method of any one of embodiments 19-25, wherein the peptide comprises from about 1 to about 30 amino acid units.
27. The method of any one of embodiments 19-26, wherein the cleavable moiety comprises phosphonium, sulfonium, and ammonium groups.
28. The method of any one of embodiments 19-26, wherein the cleavable moiety is

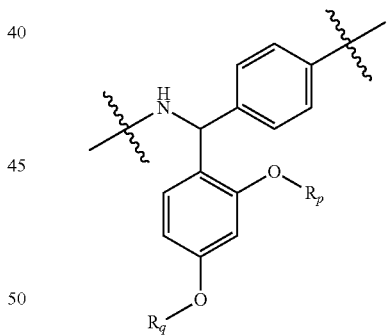

wherein each of $R_p$ and $R_q$ independently is an alkyl group.
29. A method for separating a compound from other analytes in a sample by ion mobility, comprising:
    reacting the sample to be analyzed with a first agent to chemically introduce a first ligand into the compound;
    reacting the sample to be analyzed with a second agent to chemically introduce a second ligand into the compound, thereby causing the formation of an intra-molecular complex between the first and the second ligands; and
    separating the sample by ion mobility spectrometry.
30. The method of embodiment 29, wherein the first ligand comprises a guanidinium moiety and the second ligand comprises a cyclic or non-cyclic group comprising three or more ethylene-oxide units.

31. The method of embodiment 30, wherein the first ligand is a terminal guanidinium moiety and the second ligand is a crown ether.

32. The method of embodiment 31, wherein the crown ether is selected from dibenzo-30-crown-10,30-crown-10,27-crown-9, dibenzo-27-crown-9,24-crown-8, dibenzo-24-crown-8,21-crown-7, dibenzo-21-crown-7, dibenzo-18-crown-6,18-crown-6,15-crown-5,12-crown-4, diaza-18-crown-6, and derivatives thereof.

33. The method of any one of embodiments 29-32, wherein the compound is a peptide comprising from about 1 to about 30 amino acid units.

33. A kit comprising a plurality compounds, each of the plurality of compounds has the formula of:

A-Q wherein:
A is a group comprising a first structural unit;
Q is a cyclic or non-cyclic group comprising three or more groups selected independently from oxo-hydrocarbon groups and amino-hydrocarbon groups;
wherein the plurality of compounds differ only in the A group, and the A group in each compound has a unique copy number of the first structural unit.

34. A kit comprising a plurality compounds, each of the plurality of compounds has A, Q, X, L covalently bonded sequentially in any order, as long as X is between A and L, wherein
A is a group comprising n copies of a first structural unit, wherein n is zero or an integer;
Q is a cyclic or non-cyclic group comprising three or more groups selected independently from oxo-hydrocarbon groups and amino-hydrocarbon groups;
X is a cleavable group and is optional; and
L is a group comprising m copies of a second structural unit, wherein m is zero or an integer, with the proviso that n and m are not both zero.

35. The kit of embodiment 34, wherein n is zero, and m is a different integer in each compound.

36. The kit of embodiment 34, wherein m is zero, and n is a different integer in each compound.

37. The kit of any one of embodiments 34-36, comprising no cleavable group (X).

38. The kit of embodiment 34, wherein all the compounds in the plurality of compounds have very similar or identical mass.

39. The kit of embodiment 38, wherein the sum of n and m is a constant.

40. The kit of any one of embodiments 34-39, wherein some of the compounds comprise at least two different isotopes of the same element.

41. The kit of any one of embodiments 34-40, wherein the first structural unit is the same as the second structural unit.

42. The kit of any one of embodiments 34-41, wherein the first and the second structural units are selected from the group consisting of alkylene oxide and alkylene diamine structural units.

43. The kit of any one of embodiments 34-42, wherein the first and the second structural units are selected from the group consisting of ethylene-oxide and ethylene diamine structural units.

44. The kit of any one of embodiments 34-43, wherein Q is a crown ether.

45. The kit of any one of embodiments 34-44, wherein Q is selected from dibenzo-30-crown-10,30-crown-10,27-crown-9, dibenzo-27-crown-9,24-crown-8, dibenzo-24-crown-8, 21-crown-7, dibenzo-21-crown-7, dibenzo-18-crown-6,18-crown-6,15-crown-5,12-crown-4, diaza-18-crown-6, and derivatives thereof.

46. A method of analyze multiple samples, comprising
labeling each sample with a distinct tag, which is a compound from the kit of any one of embodiments 34-45, under conditions so that at least one analyte in the sample covalently bonds to said distinct compound, wherein the analyte is capable of intra-molecular complexing with Q;
mixing the labeled samples to form a sample mix;
analyzing the sample mix by IMS.

47. The method of embodiment 47, further comprising analyzing the sample mix by MS.

48. The method of any one of embodiments 19-28, wherein the reacting step comprises reacting a plurality of original samples with a distinct compound of formula (I), and combining all the reacted original samples to form the sample.

What is claimed is:
1. A compound having the formula of

A-Q-X-L or A-X-Q-L  (I)

wherein
A is a group comprising a first repeatable monomer structural unit;
Q is a crown ether;
X is a cleavable group comprising a cleavable moiety that is cleavable via collision-induced dissociation (CID), electron-capture dissociation (ECD), electron-transfer dissociation (ETD), higher-energy collisional dissociation (HCD, or pulsed-Q dissociation (POD); and
L is a linker group comprising a second repeatable monomer structural unit.

2. The compound of claim 1, wherein the first and the second repeatable monomer structural units are selected from alkylene oxide and alkylene diamine structural units.

3. The compound of claim 1, wherein the first and the second structural units are identical.

4. The compound of claim 1, wherein the crown ether is selected from dibenzo-30-crown-10,30-crown-10,27-crown-9, dibenzo-27-crown-9,24-crown-8, dibenzo-24-crown-8, 21-crown-7, dibenzo-21-crown-7, dibenzo-18-crown-6,18-crown-6,15-crown-5,12-crown-4, diaza-18-crown-6, and derivatives thereof.

5. The compound of claim 1, wherein the cleavable moiety comprises a phosphonium, a sulfonium, or an ammonium group.

6. The compound of claim 1, wherein the cleavable moiety is

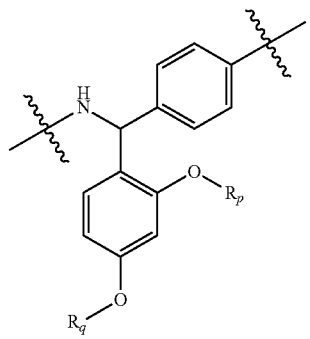

wherein each of $R_p$ and $R_q$ independently is an alkyl group.

7. A compound having the formula of

A-Q-X-L-T or A-X-Q-L-T     (II)

wherein
A is a group comprising a first repeatable monomer structural unit;
Q is a crown ether;
X is a cleavable group comprising a cleavable moiety that is cleavable via collision-induced dissociation (CID), electron-capture dissociation (ECD), electron-transfer dissociation (ETD), higher-energy collisional dissociation (HCD, or pulsed-Q dissociation (POD);
L is a linker comprising a second repeatable monomer structural unit; and
T is a peptide comprising a terminal guanidinium moiety that is capable of forming an intra-molecular complex with Q.

8. The compound of claim 7, wherein the crown ether is selected from dibenzo-30-crown-10,30-crown-10,27-crown-9, dibenzo-27-crown-9,24-crown-8, dibenzo-24-crown-8, 21-crown-7, dibenzo-21-crown-7, dibenzo-18-crown-6,18-crown-6,15-crown-5,12-crown-4, diaza-18-crown-6 and derivatives thereof.

9. The compound of claim 7, wherein
A comprises an ethylene-oxide structural unit; and
L comprises an ethylene-oxide structural unit.

10. The compound of claim 7, wherein
A comprises an ethylene diamine repeatable monomer structural unit; and
L comprises an ethylene diamine repeatable monomer structural unit.

11. The compound of claim 7, wherein the peptide comprises from about 1 to about 30 amino acid units.

12. The compound of claim 7, wherein each of A and L independently comprises from about 1 to about 20 units of the repeatable monomer structural unit.

13. The compound of claim 7, wherein the cleavable moiety comprises a phosphonium, a sulfonium, or an ammonium group.

14. The compound of claim 7, wherein the cleavable moiety is

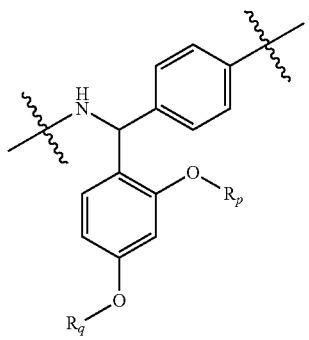

wherein each of $R_p$ and $R_q$ independently is an alkyl group.

15. A method for analyzing peptides, comprising:
reacting a sample comprising peptides with one or more compounds having the formula (I) thereby forming one or more compounds of the formula (II):

A-Q-X-L or A-X-Q-L     (I)

A-Q-X-L-T or A-X-Q-L-T     (II)

wherein
A is a group comprising a repeatable monomer structural unit;
Q is a crown ether;
X is a cleavable group comprising a cleavable moiety that is cleavable via collision-induced dissociation (CID), electron-capture dissociation (ECD), electron-transfer dissociation (ETD), higher-energy collisional dissociation (HCD, or pulsed-Q dissociation (PQD);
L is a linker comprising repeatable monomer structural unit; and
T is a peptide comprising terminal guanidinium moiety, wherein the guanidinium moiety is capable of forming intra-molecular complex with Q;
separating the formed compounds of formula (II) by ion mobility; and
causing cleavage of the cleavable group and dissociation of the compounds of formula (II) thereby forming fragments.

16. The method of claim 15, further comprising:
measuring the fragments by mass spectroscopy to analyze the peptides.

17. The method of claim 16, wherein causing cleavage of the cleavable group is via collision-induced dissociation (CID), electron-capture dissociation (ECD), electron-transfer dissociation (ETD), higher-energy collisional dissociation (HCD) or pulsed-Q dissociation (PQD).

18. The method of claim 15, further comprising, prior to reacting the sample with one or more compounds having the formula (I),
pre-treating the sample to be analyzed to chemically introduce a terminal guanidinium moiety into each peptide component in the sample not already having a guanidinium moiety.

19. The method of claim 15, wherein
A comprises an ethylene-oxide repeatable monomer unit; and
L comprises an ethylene-oxide repeatable monomer unit.

20. The method of claim 15, wherein the crown ether is selected from dibenzo-30-crown-10,30-crown-10,27-crown-9, dibenzo-27-crown-9,24-crown-8, dibenzo-24-crown-8, 21-crown-7, dibenzo-21-crown-7, dibenzo-18-crown-6,18-crown-6,15-crown-5,12-crown-4, diaza-18-crown-6, and derivatives thereof.

* * * * *